United States Patent [19]

Bohn et al.

[11] 4,424,279
[45] Jan. 3, 1984

[54] RAPID PLUNGER IMMUNOASSAY METHOD AND APPARATUS

[75] Inventors: Joseph W. Bohn; Peter A. Cohen, both of San Diego; Bruce L. Zuraw, Del Mar, all of Calif.

[73] Assignee: Quidel, La Jolla, Calif.

[21] Appl. No.: 407,454

[22] Filed: Aug. 12, 1982

[51] Int. Cl.³ .................. G01N 33/54; G01N 33/58
[52] U.S. Cl. .................. 436/534; 210/927; 210/DIG. 24; 422/61; 435/7; 435/810; 436/529; 436/533; 436/808; 436/810
[58] Field of Search .............. 435/7; 436/529, 533, 436/534, 808; 422/61; 210/927, DIG. 24

[56] References Cited

U.S. PATENT DOCUMENTS

| | | | |
|---|---|---|---|
| 3,481,477 | 12/1969 | Farr | 210/927 X |
| 3,512,940 | 5/1970 | Shapiro | 210/927 X |
| 3,661,265 | 5/1972 | Greenspan | 210/927 X |
| 3,791,932 | 2/1974 | Schuurs | 435/7 |
| 3,832,141 | 8/1974 | Haldopoulos | 210/927 X |
| 3,954,614 | 5/1976 | Wright | 210/927 X |
| 4,057,499 | 11/1977 | Buono | 210/927 X |
| 4,065,383 | 12/1977 | Skare | 210/927 X |
| 4,279,863 | 7/1981 | Friehler | 210/927 X |

Primary Examiner—Sidney Marantz
Attorney, Agent, or Firm—Hubbard & Stetina

[57] ABSTRACT

A method and apparatus for conducting an immunoassay. The apparatus features a cylindrical tube having one open end into which a plunger filter assembly is slidably fitted. The filter assembly is composed of a plunger filter cylinder open at both ends, a seal fixed to the proximal end of the plunger filter cylinder and a dome-shaped filter inside of and closing the proximal end of the plunger filter cylinder, and beads sensitized with an immunologically reactive material, such as an antibody.

12 Claims, 6 Drawing Figures

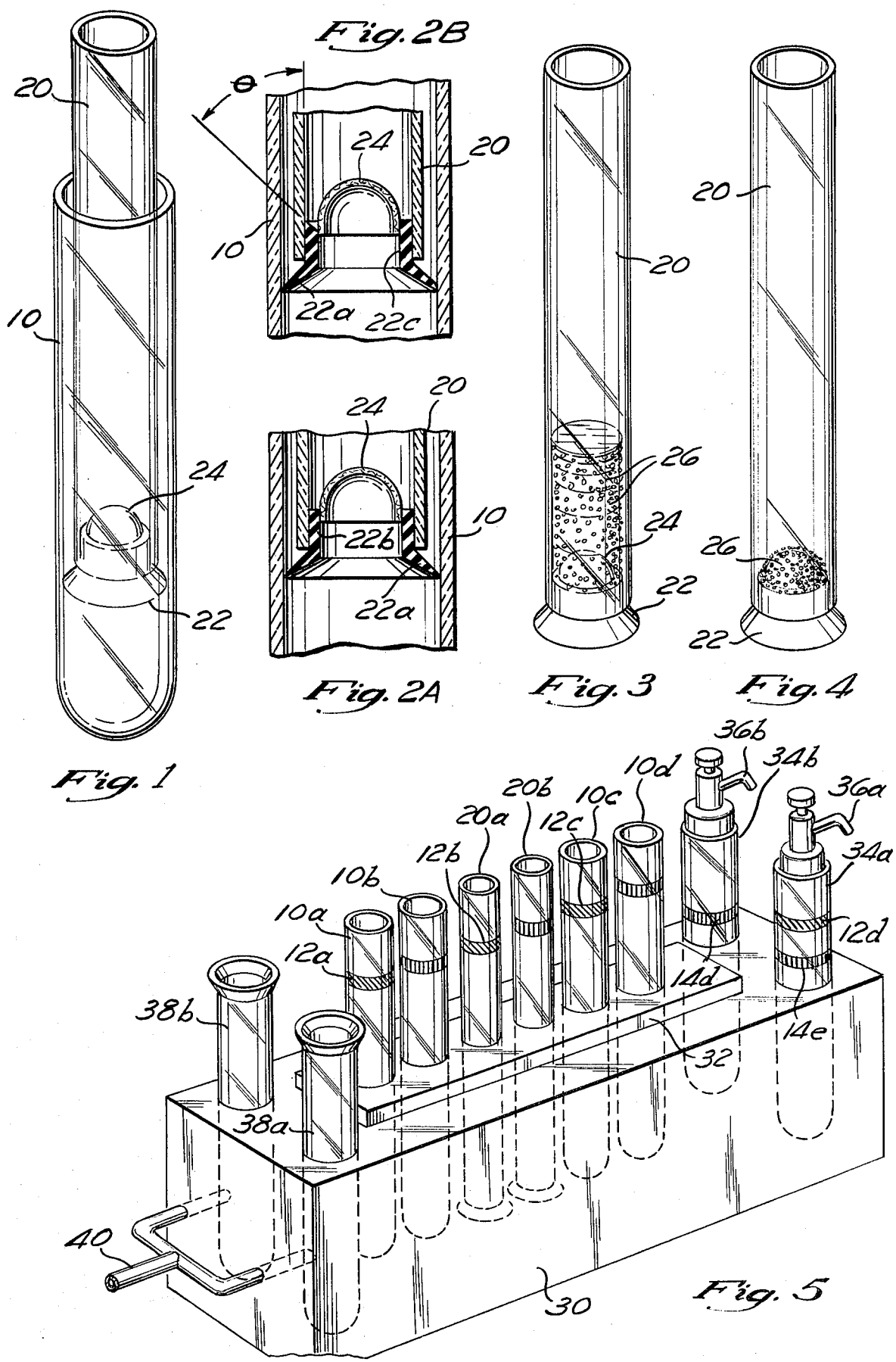

RAPID PLUNGER IMMUNOASSAY METHOD AND APPARATUS

TECHNICAL FIELD

This invention relates to immunological methods and apparatus. More specifically, this invention relates to a specific technique and apparatus for conducting an immunological assay procedure upon a fluid, such as a body fluid, or a carrier fluid, in which the immunological component to be detected is carried.

BACKGROUND OF THE INVENTION

With the advances in immunochemistry, there has been an increasing and recently accelerated need for more efficient and less expensive methods and techniques for conducting immunoassays. In many fields of endeavor in molecular biology, biochemistry, biology and genetics, it is necessary to conduct hundreds or even thousands of immunological assay procedures in order to accomplish a single result.

In the clinical treatment of immunological diseases and disorders, it is very desirable to conduct any necessary immunological assays quickly, inexpensively and efficiently in order that the time of the patient and the physician may not be wasted by long delays and repeated visits. There is, accordingly, a long-felt need for more accurate, less expensive, simpler and more efficient immunological assay procedures and apparatus for use in the physician's office or in the clinical laboratory. A large number of immunological detector mechanisms, techniques and materials have been developed over the past decade. The now classical radioimmunoassay technique is still very widely used, though it is being replaced with other techniques which use non-radioactive indicators. Enzyme linked immunoassay techniques, for example, and other photometric, fluorophotometric and colorimetric methods are also applicable to particular species of immunological components. While these advances have made the relatively rapid and accurate assay of antigens and antibodies quite feasible, the need for still more accurate, and simultaneously inexpensive and efficient apparatus and methods has gone unfilled, both in the research laboratory and in the clinical laboratory.

Existing immunoassay technologies are frequently so complicated or time-consuming that a technician is able to run only a very limited number of assays per day. On the other hand, in a clinical laboratory, as an example, the number of assays to be run during a particular day may not justify setting up and operating the apparatus for conducting the assay. Sometimes, in such circumstances, technicians allow patient samples to accumulate until there are enough samples to justify the labor of running the assay. In many clinical situations, such as in the instance of a suspected heart attack, it is distinctively detrimental to the patient if there are any delays or any inconveniences intrinsic in the assay technology. Rapid and accurate assays in such instances are vital to the health of the patient.

Among the features of this invention are methods and apparatus which overcome, fully or in large extent, all of the foregoing disadvantages of the prior art.

SUMMARY OF THE INVENTION

According to the method of the invention, a fluid which contains the immunological constituent of interest, e.g. an antigen, is introduced into a plunger filter apparatus, typically though not necessarily through the filter, and into contact with immunologically binding beads which are in the plunger filter. These immunologically binding beads bind to the immunological constituent of interest, e.g. the antigen or antibody, and extract it from the solution in which it is carried. The solution is then forced to flow out of the plunger filter, through the filter, leaving the beads in the plunger filter. The beads are washed to remove excess fluid and to retain only the immunological constituent of interest which is bound to the beads. A developer is introduced into the plunger filter which binds to the immunological constituent of interest, e.g. the antigen or antibody. Excess developer may be removed by washing, filtration, etc. Finally, the immunological constituent of interest is determined by measuring the developer according to the indicator which characterizes the developer.

As an apparatus, the invention comprises a novel improved plunger filter assembly containing beads which bind selected immunologically active constituents of the fluid to be tested, a container tube in which the plunger filter fits in a movable, fluid-tight relationship to permit fluid to be forced through the filter in either direction. Also contemplated by the apparatus is a kit including a number of such elements associated one with another in appropriate container structures to provide an apparatus complete and sufficient for the technician to run immunoassays according to this invention.

In a more specific and non-limiting sense the invention may be described as an immunoassay apparatus comprising a cylindrical container tube having an open end and a closed end, and a plunger filter assembly received in the open end of the container tube and being slidable in the container tube, the plunger filter assembly comprising a cylindrical tube open at both ends, a movable seal fixedly secured at the proximal end of the cylindrical tube, the distal end extending outwardly toward the open end of the container tube, the seal being movable with respect to the interior walls of the container tube and forming a substantially fluid tight movable seal between the proximal end of the plunger filter and the container tube, a high surface area, typically dome-shaped filter inside and closing the proximal end of the plunger filter cylinder to the passage of material in and out of said proximal end except for fluids and particles which can pass through the filter, and immunologically reactive beads which, in use, bind selected immunologically active constituents, of the fluid to be assayed, the immunologically active beads having porous surfaces treated with an immunologically active constituent and being too large to pass through the filter.

A preferred form, the filter includes pores as large as possible to permit free two-way passage of the assayed fluid and its constituents, such as blood cells, while still being small enough pored to retain the beads on one side of the filter without clogging; the filter seal comprises a skirt extending circumferentially around the plunger filter tube into movable sealing contact with the internal wall of the container tube and a sleeve securely received inside the plunger filter tube, the top of the sleeve being so constructed and arranged as to form a generally flat annular top surface which intersects with the internal wall of the plunger filter tube at an angle of not more than 90°.

Again in the preferred form, the immunologically active beads are large enough overall diameter not to pass or clog the filter, but otherwise as small as possible to slow their rate of settling, thus speeding the assay reactions. In addition, the beads should be small enough pored to prevent any antibody or developing agent from entering the interior of the beads; in this way, all coupling and reaction steps occur on the outer surface of the beads, speeding reaction time and decreasing background interference. Within this pore size constraint, the bead pore size should still be maximal to decrease the specific gravity of the beads, hence slow the rate of bead settling, and further speed assay reaction times.

In another definition the invention is an immunoassay process comprising the steps of containing a liquid assay sample in a predetermined physical configuration; forcing a filter through said configuration thereby forcing liquid sample through said filter into a second configuration into contact with a multiplicity of beads having immunologically reactive sites thereupon; maintaining the liquid in contact with said beads for a predetermined time to permit reaction of immunological constituents in the sample to react with said immunologically reactive sites on said beads; withdrawing the filter from the configuration thereby forcing liquid sample through the filter out of the second configuration out of contact with te beads; washing residual liquid from the beads; determining the reaction of immunological constituents from the sample with the immunologically reactive sites on the beads.

In a preferred form the determination step comprises removing immunological constituents from the beads into liquid in said second configuration, reacting said constituents with an indicator, and determining the presence of indicator in said liquid in the second configuration as a measure of the amount of immunological constituent in the sample.

BRIEF DESCRIPTION OF THE DRAWINGS

FIG. 1 is a perspective view of the basic structure of the apparatus of this invention.

FIG. 2A is a cross-sectional view showing in detail the structure of the lower part of the plunger filter, including the filter, the movable seal, the bottom of the plunger filter tube and the container tube.

FIG. 2B depicts an alternative embodiment of the seal as shown in FIG. 2A.

FIG. 3 is a perspective view of a plunger filter with a fluid contained therein during extraction of the immunological component from the fluid onto the beads.

FIG. 4 is the same plunger filter but with the fluid removed, the beads being retained on the filter.

FIG. 5 is a perspective view of a kit embodying the concept and principle of the invention.

DESCRIPTION OF THE BEST MODE

In the following description, the apparatus and the method will be described, in exemplary terms only, for an antigen-determining immunoassay test. This discussion, however, is simply to illustrate the structure and use of the apparatus and the technique and steps of the method. Parallel steps and uses of the apparatus would be involved in any immunological component determination using the particular developer of choice for that particular immunological assay. For example, a bound enzyme detection technique will be described. Clearly, immunofluorescent, RIA and other techniques, as well as ELISA techniques, may be used. The best mode, as described hereinafter, is, accordingly, to be considered exemplary and not limiting as to the scope and concept of the invention.

The Apparatus

Referring first to FIG. 1, for a general depiction of the apparatus, the inventive apparatus comprises a container tube 10 which typically is in the form of a conventional cylindrical tube with a round bottom, often referred to as a test tube. The essential reaction vessel is a plastic cylinder 20, to which a removable seal 22 is affixed which seals the space between the tube 20 and the container tube 10 when the former is inserted in the latter. The reaction vessel also comprises a filter 24 and beads 26, the latter being shown better in FIGS. 3 and 4. The combination of the tube 20, the seal 22 and the filter 24, which contains the beads 26, is referred to as a plunger-filter.

The construction of the seal 22 and the filter 24 is somewhat critical. Reference is made to FIG. 2A for details of this construction. The seal 22 comprises an insert sleeve 22a, which is in fluid-tight relationship on the interior of the tube 20 and a skirt 22b which extends outwardly around the circumference of the tube 20 into contact with the inner walls of the tube 10 forming a movable, fluid-tight seal between the tube 20 and the tube 10. The skirt is resilient, and preferrably, is made of a resilient rubber or polymer. The sleeve 22a is typically also made of the same resilient material and 22a and 22b are typically a unitary body, although this is not essential. The sleeve 22a may, for example, be comparatively rigid and be adhesively, or otherwise, sealed or secured in the tube 20. It is important that the upper portion of the sleeve 22 be constructed in such a manner as to preclude the entrapping or retention of any particles. In the particular embodiment shown, it has been found that when the top of the sleeve 22b extends at right angles, or approximately right angles, from the wall of tube 20, there is no significant entrapment of particles.

An alternative embodiment is shown in FIG. 2B, in which the sleeve 22c has an upper edge which slopes downward inwardly toward the filter 24. Similarly, there is no entrapment of particles in this arrangement. Thus, with particular reference to FIG. 2B, a single angle between the interior wall of the cylinder 20 and the top surface of the shoulder of the seal 22 is 90° or less.

In addition, it is critical that the upper edge of sleeve 22 make firm physical contact with the filter. This permits downward suction to be applied through the filter which can quantitatively remove all fluid in the filter-plunger. Without this firm contact of sleeve 22 to filter 24, pockets of fluid are retained on sleeve 22 despite all suction efforts and wash steps are poorly efficient.

In practice, it has been found that the right-angle relationship between the interior wall of the cylinder 20 and the top of the sleeve of seal 22 has been found to be most advantageous, notwithstanding that there are some theoretical advantages to having the angle less than 90°. In practice, the 90° angle provides a strong sealing relationship, is conveniently assembled, and quite adequately prevents the entrapment of particles.

Antibody covalently coupled to beads 26 are placed in the plunger-filter and will be retained in the plunger-filter even if suction is applied downwardly through the filter, because the size of the particles is such that they cannot pass through the filter. An important filter characteristic is that it possess a high surface area, typically a domed surface, so as to maximize suction efficiency even while beads are pulled down snugly upon it.

The apparatus, in kit form, comprises the same essential components with additional components for convenience in carrying out the immunoassay. The kit will be described hereinafter.

The Method

The basic immunological reaction, in an exemplary form, is described as follows. An antibody with specificity for a "test antigen" is covalently coupled to the beads. The beads, to which the antibody is coupled, are retained in the plunger-filter. These "antibody-beads" are resuspended, during use, within the plunger-filter in the presence of the biological fluids or other fluids to be assayed for the "test antigen". At the same time, or subsequently, the antibody-beads are incubated in a solution containing a "second antibody-enzyme". This second antibody-enzyme also has specificity for the test antigen and, in addition, is covalently coupled to an enzyme. If the test antigen is present in the assayed biological or other fluid, it will bind to both antibodies. Some of the test antigen will be bound simultaneously to the antibody bead and to the second antibody enzyme. In this way, the second antibody enzyme is bound to the beads and is retained on the beads through the highly specific immunological reaction. The antibody beads, with the antigen and the antibody-enzyme bound thereto, are then washed by vacuum suction applied at the filter base, by introducing the wash solution into the plunger-filter and pulling the plunger-filter up, as shown in the Figures, in the cylindrical container tube 10 to force the wash solution through the filter. Finally, the beads are re-suspended in a "developing substrate solution". The enzyme, coupled to the second antibody, alters the substrate and results in a color change, or some other detectable phenomena. The developing solution will, in the colorimetric method, change color visibly, or in the ultraviolet or infrared range, and this color change can be detected either visually or by use of appropriate ultraviolet or infrared photometric instruments. The change, per se, constitutes a quantitative indication of the presence of the test antigen. The amount of the change in the developing solution, e.g. the intensity of the color, the intensity of the radiation, etc., is a quantitative indicator of the amount of the test antigen in the assayed fluid.

It will be noted that the above description is an adaptation of a known antibody enzyme-linked immunoassay to the plunger-filter system of this invention, and is given merely as an example.

By having a "first antibody" present on suspendable small beads, rather than on a flat surface, a very much greater random interface is rapidly achieved between the antibody and the test antigen. Since the antibody will more frequently "see" the test antigen, the reaction time is much faster and the reaction goes much further to completion. It has been shown that if the beads are kept in suspension during incubation, an incubation time of under 15 minutes can result in immunoassays with at least nanogram/milliliter sensitivity. This compares with immunoassays which require several hours if the first antibody is attached only to a flat surface.

Another important advantage is that centrifugations are avoided entirely. The liquid can be evacuated from the plunger by suction, with the antibody beads being retained within the plunger filter.

Filter plungers are currently manufactured for a single clinical use, the collection of serum or plasma from patient blood. When blood is centrifuged, the blood cells are spun down to the bottom of the tube, leaving the plasma-serum at the top. Filter plungers are inserted into the tubes, stopping short of the blood cells, enabling serum-plasma to pass into the plunger. The filter prevents clots and other particulate debris from entering the plunger. None of the currently manufactured filter-plungers are, however, suitable for assay according to this invention. To achieve an assay of high sensitivity, short reaction time, and low color background, the conditions of bead size and bead porosity, filter pore size, plunger geometry, and fluid density during the antibody-antigen reaction are very significant. In addition, the present invention permits direct immunoassay of whole blood, as opposed to conventionally assayed serum or plasma. These various facets of the invention are now discussed.

Using carefully defined filter and bead dimensions, it is possible to assay anti-coagulated whole blood. This eliminates a time-consuming chore of preparing plasma or serum from blood. To assay whole blood, plungers are fitted with filters of effective 15-17 micron pore size. Since normal blood cells are all smaller than 15 microns in diameter, they can pass freely through the filter into the plunger-filter which defines the reaction chamber to begin the antibody-antigen reaction, then pass freely out through the filter at the end of the reaction, leaving the antibody beads behind. Hemolysis is minimal. The antibody beads are chosen to be sufficiently larger than the filter pores so that they are retained by and do not clog the filter. It has been found that crosslinked dextran beads of 20-30 micron swollen diameter, with swollen bead pore size excluding proteins larger than 30,000-70,000 Daltons, are quite suitable for this purpose. Such beads are small and porous enough to remain largely in suspension without mechanical means during the reaction steps, as opposed to beads 35 microns or larger. Similar sized beads of polyacrylamide are also suitable for this type of assay. The bead types defined here are exemplary only; other bead sources are also suitable.

To run a reaction on whole blood optimally, a filter with a pore size just large enough to let the blood cells pass freely, but small enough to retain the beads which are not so small as to clog the filter but themselves are as small as possible to better remain in suspension during incubations, is required. Less than optimal results may, of course, be achieved using smaller beads even though some modest clogging may result or larger beads which will tend to settle, if time, stirring, shaking, or other accommodation is made to overcome these particular disadvantages.

The beads should be porous enough to slow bead settling, thereby speeding assay reactions, but still be small enough pored to prevent antibody and developing agent molecule from entering the beads. Crosslinked dextran beads with swollen pore size excluding proteins larger than 30,000-70,000 Daltons are suitable for these purposes, showing good buoyancy while still excluding larger proteins such as antibodies from their interiors. Similar sized polyacrylamide beads are also suitable, and these bead types are exemplary only. This carefully defined bead geometry in regards to diameter and pore size is critical to this assay's rapidity and sensitivity. The bead pores are small enough to ensure that all immunological reagents coupled to the beads are present on the outer surface of the beads. This speeds the assay reactions since the test antigen does not have to migrate into the beads to interface with antibody bound to the beads. Simultaneously, the invention's defined bead geometry shows much less bead settling over time than larger diameter or small pored beads, this feature greatly enhancing assay rapidity. Finally, the pore size excludes second antibody-enzyme or other developing agents from entering the beads. Larger pored beads such as Sepharose (Trademark) permit second antibody-enzyme to enter the beads, to remain nonspecifically trapped during wash steps, and finally to cause unwanted high background interference during development. The defined bead geometry of this invention eliminates this source of assay background interference.

In currently manufactured filter plungers, the filter is held in place by a rubber ring entrapment. If the rubber ring bulges around the filter on the inside of the plunger, it causes unwanted fluid retention even after exhaustive suction has been applied. It has been shown that by reshaping the rubber rings so that the filter protrudes freely well above the rubber into the plunger-filter, the antibody beads, or other immunological reagent-bound beads, can be sucked completely dry during the wash steps. It is essential that the beads be sucked fully dry during each wash, if one is to achieve a quantitative washout of the enzyme which is not specifically bound to the beads. According to the present invention, plungers are designed to achieve this effect. This is an important change in the plunger design. In addition, by increasing the exposed surface area of the filter inside the plunger-filter assembly, a very much more effective suction can be applied. Without this design alteration, it is, for all practical purposes, virtually impossible to wash small-mesh beads effectively.

It has also been found to be important that the rubber ring make contact with the inside of the plunger filter cylinder at a 90° angle or less, referring to angle $\phi$ in FIGS. 2A and 2B. If the contact angle is greater than 90°, a crevice occurs in which the blood cells become trapped. These blood cells cannot be completely removed during the wash and hemolysis may cause a very greatly increased background in the final developing stage of the assay. Reshaping the rubber to make it perpendicular in its contact with the interior of the tube 20 eliminates blood cell entrapment and carryover. An alternative, but somewhat less preferred, approach is to make the contact less than 90°.

The first stage incubation, during which the antibody beads are reacted with the test antigen, proceeds faster if the beads are evenly dispersed in the incubation fluid. It is, therefore, highly desirable to avoid the settling of the beads. This can be achieved by rocking, stirring or agitating the plunger-filter assemblies during the reaction. This may be done by hand or automatically by appropriate rocking equipment. However, according to this invention, even this inconvenience is avoided by carefully preselecting bead size and porosity to minimize settling while still permitting bead retention by the filter. In addition, certain carrier substances are of sufficient density and possess appropriate charge properties further to prevent the settling of antibody beads. Carriers such as casein and albumin are suitable for many assays. Other densifying carriers may also be used. It should be noted that in assays of whole blood there is little or no need of any additional carrier since the density of the blood itself is usually sufficiently high to prevent settling or at least to provide for very slow settling of the beads.

Another important feature of this invention is the use of cleavable cross-linking agents to couple the second antibody to the enzyme. This permits rapid liberation of the enzyme from the beads by introduction of a reducing agent, during development, to cleave the enzyme from the antibody, leaving the enzyme in solution and capable of reacting with the developing solution to provide the color or other indicator result. Liberation of the enzyme into the liquid phase greatly speeds the color reaction, and permits the enzyme to pass through the plunger-filter into a fresh reading tube. Thus, according to this approach, the developed solution in the plunger-filter tube may be quantitatively transferred from the plunger-filter tube into a container tube, simply by drawing a vacuum suction through the filter, drawing the developed solution into the container tube.

There are other important features of the invention as well. It has been shown that nonionic detergents provide for more complete washing of the unbound enzyme from the plunger-filter tube, resulting in a lower background. Nonionic detergents do not impair enzyme activity or antigen-antibody reactions present during the wash stages. In addition, they promote lysis and removal of any blood cells retained in the plunger. Sometimes, foaming occurs when nonionic detergents are used. Excessive foaming may be prevented by adding minute amounts of anti-foaming agents. Anti-foaming agents have been shown not to impair the enzyme activity during the wash steps.

Coated plunger-filter surfaces have also been found to be advantageous. Coating the surface with polytetrafluroethylene (Teflon: a trademark of DuPont), silicone lubricants, acrylic lubricants, or other various coatings, alters the inner surface properties of the plunger-filter, and may result in less sticking of beads to the inner walls of the plunger-filter. Such treatments also reduce unwanted sticking of the second antibody-enzyme, thus reducing background.

The foregoing technique is broadly applicable to biological fluids of virtually any type. The technique is also applicable to other fluids, and to other types of bioassays, quite obviously. For example, if it is desired to assay exudates, secretions, fecal materials, etc., the technique is very easily and effectively adapted to such an approach. A soft, inert, easily compressible material, such as silicone foam or a resolubilizable calcium alginate swab, etc., mounted on a detachable plastic or cardboard "swab" stick, is wiped on the area to be tested, such as the pharynx, rectum, and the stick is then detached from the sponge ball, which is dropped into an appropriately sized container tube. The plunger, containing antibody beads, is then pressed against the test tube as far as possible, bearing down forcefully on a sponge ball. With fluid covering the sponge ball, the sponge ball may be "pumped" a number of times. When strongly compressed one time or repeatedly in a pumping approach, the biological fluid is expressed out of the ball and then is carried with the solution through the filter into the plunger-filter assembly. When assays are run on these types of materials rather than whole blood, the filter porosity can be very much smaller than 20 microns, and the bead size may be commensurately smaller, thus resulting in a slower bead settling.

The technique of this invention may, as earlier indicated, be applied to virtually any type of immunoassay.

For example, it may be used to carry out immunocompetition assays.

While antibody beads have been used for some time in immunological assays (see, for example, Richman, Douglas D., et al, "The Binding of Staphylococcal Protein A By the Sera of Different Animal Species", *Journal of Immunology*, Vol. 128, No. 5, 1982), the plunger-filter construction and technique described hereinbefore is believed to be entirely novel and to be highly advantageous over all known prior techniques and apparatus. The plunger-filter apparatus of this invention is entirely new and its use as systems for assays not involving radioactivity or simply to eliminate more steps is novel. Particularly, its usefulness in reducing reaction time by hours is a new concept and approach in the art. As described above, the existing plunger technology as well as reagent and sample handling, have been greatly improved to achieve the particular ends of high sensitivity, rapid reaction time, convenience, low cost, and low background development.

The invention, as described hereinbefore, includes a number of advantageous features. First is the use of enzyme-linked assay in a plunger-filter system, which provides extremely high sensitivity coupled with low cost and high efficiency and a short time delay. The deliberate use of antibody-beads rather than antibody on a flat phase to increase the reaction surface area accelerates reaction time. Combining the use of beads with the plunger-filter system further reduces the time in running an assay. The balancing of the necessary properties of the filter and the beads to reduce bead settling during incubation of the assay very much shorten incubation time with great and unexpected advantages over the prior art. The deliberate choice of slow settling beads still small pored enough to prevent the entrance of a developing reagent, e.g. a second antibody-enzyme, and to hasten encounters between the antigen and the developing reagent, has also proven to be a very great advance, reducing time and increasing sensitivity of the assay. The design of the plunger-filter to eliminate fluid and cell retention is also regarded as a very important feature of the invention. Effective wash suction cannot be applied to the plunger-filter with the prior art device.

The features include the optional use of a specific gravity increasing carrier, such as albumin, to keep the beads in suspension. The reducible cross-linking enzyme on the second antibody-enzyme conjugate is also highly advantageous so that the enzyme can be liberated from the beads and color development, or other development reaction, can proceed in a clean tube, is also significant. The use of nonionic detergents and anti-foam agents is a further advantage in the use of a coating to prevent sticking of the beads to the interior wall of the plunger-filter.

A very distinct and important advantage of the present invention is that it can be used to assay whole, uncoagulated, blood and carrier solutions, as well as biological materials. Another advantage is that the technique and apparatus of this invention can be used to run virtually any kind of immunological assay.

Kit Apparatus

For certain assays, such as testing for the presence of a certain type of bacterial antigen in the throat, the physician is not interested in any quantitative measure, and only a qualitative result is significant. In other situations, for example in the case of a heart attack where an indicating protein will be found in the blood as a measure of the seriousness of the heart attack, the physician is interested in both the presence and the amount of the protein and, thus, quantitative results are important. In the latter instance, for example, time is also extremely important and the physician simply cannot wait for many hours or days before beginning treatment.

The kit depicted in FIG. 5 is particularly advantageous in providing the physician or the clinical laboratory with a very quick, efficient apparatus for conducting small numbers of assays at low cost and with very short time delay. A base 30 is usually provided, in a convenient form of the kit invention, to hold the kit which a base receives a holder 32, which may be of any design, which holds a number of container tubes 10 and plunger-filter assemblies 20. In a particular embodiment, the holder 32 includes four container tubes, two for use as a standard or reference, and two for running the assay on the biological fluid. The kit typically also includes two plunger-filters, one for the standard or reference and one for the assay. In a preferred embodiment, the reference containers and plunger-filter assemblies, the reference containers and plunger-filter assemblies are color coded as shown at 12a, 12b, and 12c in, for example, green, whereas the antigen test components are color coded in red as shown at 14a, 14b, and 14c, in FIG. 5. A number, usually two or more, reagent dispensers 34a and 34b, typically equipped with a reagent pump 36a and 36b, are also provided. These are color coded in a like manner with a green code at 12d and a red at 14d and 14e.

A pair of vacuum cups 38a and 38b, connected through a communicating conduit to 40, which is attached, in use, to a vacuum supply, are provided for convenient washing and removal of liquids from the plunger-filter assembly are also provided.

The base 30 may be either permanent or temporary. For example, it may be made of wood or metal, or it may be temporary, made of cardboard or styrofoam. The base has a number of receptacles into which either individual container tubes and plunger-filter apparatus may be inserted or into which a kit component such as 32, which contains the container tubes and the plunger-filter assemblies, may be inserted. The base also, typically, would provide for a number of reagent dispensers and, of course, would provide for the vacuum cups. The base may be designed to include a number of kits, for example, the base may include a number of receptacles for including two, three or more kits, as desired.

Using, simply as an example and not in any limiting sense, a kit containing fifteen test runs, each kit would include a number of holders, each with a set of, for example, six tubes in their proper relationship, shown in FIG. 5. The holder 32 would contain all of the tubes necessary to run a single patient assay.

Referring to FIG. 5, and the kit 32 including the tubes and plunger-filters therein, one tube 10a is color coded, e.g. green, and is a clean test tube in which the standard control will be assayed. The second tube, 10b, color coded another color, e.g. red, is a clean test tube in which the patient's blood or other fluid is to be assayed. If whole blood, tube 10b may be a vacutainer type blood collection tube, the type conventionally used in the collection of blood samples.

20a is a plunger-filter containing antibody beads in a buffer with a suitable preservative. It is filled to the top and capped securely.

Tube 20b is identical to tube 20a, except that tube 20a is color coded green as shown at 12c and tube 20b is color coded red as shown at 14c. The container tube 10c is a clean, green color coded test tube in which the standard control will finally be read. Tube 10d is identical to tube 10c, except that it is color coded red for reading the fluid assay. In addition to the foregoing portion of the kit, the kit will include reagent dispensers. These dispensers will contain the necessary stock solutions, such as the second antibody-enzyme or control standards. They will have color codings to indicate whether the solution therein is to be dispensed into the red tubes, or the green tubes, or into both. In the particular embodiment, which is merely exemplary, the reagent dispenser 34a is designed to dispense into both the green and the red tubes whereas the reagent dispenser 34b dispenses only into the red tubes. Quite obviously, any number of color codings to meet the particular needs of the particular assay may be provided.

The kit may also include other dispensers, such as an eyedrop bottle which will contain a stop solution. Extra bottles, e.g. a wash bottle, etc., may also be included in the kit.

In carrying out a particular immunological assay, which is merely exemplary, the six tubes in the kit holder 32 are inserted in the cavity in the base 30. If the base is adapted to receive more than one kit, any number of kits receivable within the base may be inserted therein.

The patient's sample, or other biological fluid to be assayed, is added to tube 10b up to a level which may be predetermined. Alternatively, if tube 10b is a vacutainer type blood collection tube, the vacuum in it will be such as to collect the exact amount of blood used in the assay, to which an appropriate volume of an anti-coagulant, such as EDTA or heparin, would be added or present.

Reagents would be squirted, as indicated by the color coding, into tubes indicated by the color coding into tubes 10a and 10b. Tube 10b would receive both a second antibody-enzyme and a standard. Tube 10c would receive only the second antibody-enzyme. The two plunger-filters 20a and 20b would be uncapped, placed on the vacuum receptacles, and the beads sucked dry. The plungers then would be inserted into the appropriately colored tubes 10a and 10b. In so doing, the blood or other biological solution in one tube and the standard in the other is forced up through the filter in the plunger-filter, resuspending the antibody beads and initiating the reaction. The beads are maintained in suspension by any of a number of different means, including the use of high density carrier substances such as albumin, or simply by mechanically rocking or agitating.

At the end of the reaction time, which is usually only 15 or 20 minutes, the plungers are withdrawn from the tubes and placed in the vacuum receptacles 30a and 30b, which are attached in fluid communication relationship with any source of vacuum. The tubes 10a and 10b may then be discarded. The beads within the plungers 20a and 20b are then washed the desired number of times with a suitable wash solution, which may be provided as part of the kit or may be simply a standard stock solution available in the laboratory. The washing removes blood cells and enzymes which are not specifically bound to the beads. The vacuum sucks the wash solutions through the beads and through the filter. Now, the plunger-filters are then inserted in the appropriately colored tubes 10c and 10d and the plungers are inserted down to the predetermined position. Developing solution, in a predetermined quantity usually, though not necessarily, is then introduced into the plunger-filters according to the particular immunoassay that has to be done. If a reducing agent is used, the reducing agent in the solution liberates the enzyme from the beads, permitting the enzyme to pass through the filter of the plunger-filter. After an appropriate period of time, the plungers are pulled out of these tubes, creating a vacuum which sucks the developing solution which is carrying the enzyme into the respective tubes 10c and 10d. The plungers may then be discarded. The tubes 10c and 10d are then measured, either by visual color change, or spectrophotometrically, or by any other desired detecting means. Qualitative differences, in the colorimetric, may be assessed by eye or by colorimeter. Quantitative differences will normally be determined by any suitable instrument such as a photometer, a beta or gamma counter, etc. The tubes 10 may be of a size and configuration to be received directly into the cell chambers of commercially available photometers or colorimeters. Depending upon the particular immunoassay being run, the color change, or other detecting reaction, can be arrested by a stop solution.

In large-volume laboratories, it is entirely feasible to construct a quantitative reading device, such as a colorimeter or photometer which is designed to accept container tubes of any particular or desired configuration. This is convenient in certain laboratories but, of course, is not a part of the present invention.

INDUSTRIAL APPLICATION

The apparatus and methods of this invention are adapted for use in industrial, research, scientific and clinical laboratories generally, wherever any type of immunological assay is run. The invention provides highly efficient, high sensitivity, low cost immunoassay techniques and apparatus.

What is claimed is:

1. An immunoassay apparatus comprising:
   a cylindrical container tube having an open end and a closed end;
   a plunger filter assembly received in the open end of the container tube and being slidable in the container tube; and
   the plunger filter assembly comprising a cylindrical tube open at both ends, a movable seal fixedly secured at the proximal end of the cylindrical tube, the distal end extending outwardly toward the open end of the container tube, the seal being movable with respect to the interior walls of the container tube and forming a substantially fluid tight movable seal between the proximal end of the plunger filter and the container tube, a dome-shaped filter inside and closing the proximal end of the plunger filter cylinder to the passage of material in and out of said proximal end except for fluids and particles which can pass through the filter, and immunologically reactive beads which, in use, bind selected immunologically active constituents, of the fluid to be assayed, the immunologically active beads having porous surfaces treated with an immunologically active constituent and being too large to pass through the filter.

2. The apparatus of claim 1 where the filter includes pores large enough to permit free two-way passage of assayed fluid constituents, such as blood cells, but pores still small enough to retain slow-settling beads on one side of the filter.

3. The apparatus of claim 1 or claim 2 wherein the seal comprises a skirt extending circumferentially around the plunger filter tube into movable sealing contact with the internal wall of the container tube and a sleeve securely received inside the plunger filter tube, the top of the sleeve being so constructed and arranged as to form a generally flat annular top surface with intersects with the internal wall of the plunger filter tube at an angle of not more than 90°.

4. The apparatus of claim 4 wherein the angle is approximately 90°.

5. The apparatus of claims 1, 2, 3 or 4 wherein the beads possess a pore size excluding immunological and developing molecules, but otherwise manifesting maximal porosity and minimal overall bead size to promote buoyancy and slow bead settling, while still being retained on one side of the filter.

6. A kit for carrying out an immunological assay comprising:

a plurality of container tubes, each of said container tubes being generally cylindrical;

a plurality of plunger filter assemblies, each of said plunger filter assemblies comprising a cylindrical tube open at both ends, a movable seal fixedly secured at the proximal end of the cylindrical tube, the distal end extending outwardly toward the open end of the container tube, the seal being movable with respect to the interior walls of the container tube and forming a substantially fluid tight movable seal between the proximal end of the plunger filter and the container tube, a high surface area filter inside and closing the proximal end of the plunger filter cylinder to the passage of material in and out of said proximal end except for fluids and particles which can pass through the filter, and immunologically reactive beads which, in use, bind selected immunologically active constituents, of the fluid to be assayed, the immunologically active beads having porous surfaces treated with an immunologically active constituent and being too large to pass through the filter; and a plurality of dispensers for reagent and wash solutions.

7. The apparatus of claim 6 wherein the filter includes pores large enough to permit free two-way passage of assayed fluid constituents, such as blood cells, but pores still small enough to retain slow-settling beads on one side of the filter.

8. The apparatus of claim 6 or claim 7 wherein the seal comprises a skirt extending circumferentially around the plunger filter tube into movable sealing contact with the internal wall of the container tube and a sleeve securely received inside the plunger filter tube, the top of the sleeve being so constructed and arranged as to form a generally flat annular top surface which intersects with the internal wall of the plunger filter tube at an angle of not more than 90°.

9. The apparatus of claim 8 wherein the angle is approximately 90°.

10. The apparatus of claims 6, 7, 8 or 9 wherein the beads possess a pore size excluding immunological and developing molecules, but otherwise manifesting maximal porosity and minimal overall bead size to promote buoyancy and slow bead settling, while still being retained on one side of the filter.

11. An immunoassay process comprising the steps of:

containing a liquid assay sample in a predetermined physical configuration;

forcing a filter through said configuration thereby forcing liquid sample through said filter into a second configuration into contact with a multiplicity of beads having immunologically reactive sites thereupon;

maintaining the liquid in contact with said beads for a predetermined time to permit reaction of immunological constituents in the sample to react with said immunologically reactive sites on said beads;

withdrawing the filter from the configuration thereby forcing liquid sample through the filter out of the second configuration out of contact with the beads;

washing residual liquid from the beads;

determining the reaction of immunological constituents from the sample with the immunologically reactive sites on the beads.

12. The process of claim 11 wherein the determination step comprises:

removing immunological constituents from the beads into liquid in said second configuration, reacting said constituents with an indicator, and determining the presence of indicator in said liquid in the second configuration as measure of the amount of immunological constituent in the sample.

* * * * *